United States Patent
Upshaw et al.

(10) Patent No.: US 7,566,802 B2
(45) Date of Patent: Jul. 28, 2009

(54) PROCESS FOR ENERGY RECOVERY AND WATER REMOVAL IN THE PREPARATION OF AROMATIC CARBOXYLIC ACIDS

(75) Inventors: Timothy Alan Upshaw, Kingsport, TN (US); Ronald Buford Sheppard, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 203 days.

(21) Appl. No.: 11/440,187

(22) Filed: May 24, 2006

(65) Prior Publication Data

US 2007/0276155 A1 Nov. 29, 2007

(51) Int. Cl.
*C07C 51/16* (2006.01)
(52) U.S. Cl. .................... 562/412; 562/409; 562/416
(58) Field of Classification Search ............ 562/412, 562/409, 416
See application file for complete search history.

(56) References Cited

U.S. PATENT DOCUMENTS

| | | | |
|---|---|---|---|
| 3,996,271 A | 12/1976 | Yokota et al. | |
| 4,158,738 A | 6/1979 | Scott et al. | |
| 5,510,521 A | 4/1996 | McGehee et al. | |
| 5,723,565 A | 3/1998 | Cuscurida et al. | |
| 5,723,656 A * | 3/1998 | Abrams | 562/412 |

FOREIGN PATENT DOCUMENTS

| | | |
|---|---|---|
| EP | 0 962 442 A1 | 12/1999 |
| JP | 56-040636 | 4/1981 |
| WO | WO 02/098833 A1 | 12/2002 |
| WO | WO 2006/102137 A1 | 9/2006 |

OTHER PUBLICATIONS

Reumers, "Energy Conservation at Amoco Chemicals," Journal A, vol. 25 (3), 1984.
Notification of Transmittal of the International Search Report and the Written Opinion of the International Searching Authority, or the Declaration date of mailing Nov. 7, 2007 on PCT/US2007/011351.

* cited by examiner

*Primary Examiner*—Jafar Parsa
*Assistant Examiner*—Sudhakar Katakam
(74) *Attorney, Agent, or Firm*—Brett L Nelson; Bernard J. Graves, Jr.

(57) ABSTRACT

This invention relates to a process for the manufacture of aromatic carboxylic acids by exothermic liquid phase oxidation of an aromatic feedstock. More particularly, this invention relates to the efficient energy recovery of the exotherm produced by the liquid phase oxidation of an aromatic feedstock. Also, this invention relates to the efficient energy recovery of the exotherm produced by the liquid phase oxidation of an aromatic feedstock while also utilizing the heat from the energy of oxidation to efficiently remove water resulting from the exothermic oxidation reaction.

56 Claims, 2 Drawing Sheets

PROCESS FOR ENERGY RECOVERY AND WATER REMOVAL IN THE PREPARATION OF AROMATIC CARBOXYLIC ACIDS

FIELD OF THE INVENTION

This invention relates to a process for the manufacture of an aromatic carboxylic acid composition by exothermic liquid phase oxidation of an aromatic feedstock composition. More particularly, this invention relates to the efficient energy recovery of the exotherm produced by the liquid phase oxidation of an aromatic feedstock composition and the efficient removal of the water resulting from the liquid phase oxidation.

BACKGROUND OF THE INVENTION

Aromatic carboxylic acids, such as terephthalic acid, isophthalic acid, and napthlene dicarboxylic acid are useful chemical compounds and are raw materials in the production of polyesters. In the instance of terephthalic acid, a single manufacturing facility can produce greater than 100,000 metric tons per annum as feedstock for a polyethylene terephthalate (PET) facility.

Terephthalic acid (TPA) may be produced by the high pressure, exothermic oxidation of a suitable aromatic feedstock such as para-xylene. Typically, these oxidations are carried out in a liquid phase using air or alternate sources of molecular oxygen in the presence of a metal catalyst or promoter compound(s). Methods for oxidizing para-xylene and other aromatic compounds such as m-xylene and dimethylnaphthalene are well known in the art. These oxidation reactions will typically produce reaction gases generally comprising oxidation reaction products such as carbon monoxide, carbon dioxide, and methyl bromide. Additionally, if air is used as the oxygen source, the reaction gases may also comprise nitrogen and excess oxygen.

Some processes for the production of TPA also employ a low molecular weight carboxylic acid, such as acetic acid, as part of the reaction solvent. Additionally, some water may also be present in the oxidation solvent as well as being formed as an oxidation by-product.

Oxidations of this type are generally highly exothermic, and although there are many ways to control the temperature of these reactions, a common and convenient method is to remove the heat by allowing a portion of the solvent to vaporize during the reaction. The combination of the reaction gases and the vaporized solvent is sometimes referred to as oxidation reaction offgas. The oxidation reaction offgas contains a considerable amount of energy, and it is often desirable to efficiently recover energy contained in the offgas.

For example, JP 56-40636A describes an "oxidation reaction waste gas" as containing large amounts of moisture and vaporized aliphatic carboxylic acids, and also containing a small amount of bromine which all have corrosive properties. And although JP 56-40636A subsequently indicates that corrosion related problems can be avoided by constructing equipment from titanium or another corrosion resistant material, there are other examples of workers who have avoided corrosion issues by removing some or all of the components of the oxidation reaction offgas prior to introduction into a power recovery device.

In an article by Reumers, "Energy Conservation at Amoco Chemicals", Journal A, Vol. 25 (3), 1984, an oxidation reactor offgas is passed to a condenser to remove the condensable components (i.e. low molecular weight carboxylic acid and water) and thus form an offgas comprising primarily nitrogen. The condenser offgas, which is composed almost exclusively of noncondensing gas or gases, is then passed to a turboexpander for energy recovery. In U.S. Pat. No. 5,723,656, an oxidation reactor offgas is passed to a high efficiency separation apparatus which removes most of the reaction solvent from the oxidizer offgas prior to directing to the resulting gaseous product which contains water vapor to a turboexpander.

Also in some processes for the manufacture of aromatic carboxylic acid, for example terephthalic acid, a desirable result is the efficient removal of the excess water generated by the exothermic liquid phase oxidation. It is usually desirable to maintain a consistently low water concentration, typically below 10 weight percent, in the oxidation reaction zone for the oxidation reaction to continue at a reasonable rate. The primary oxidation reaction produces one mole of water per mole of carboxyl moiety produced. In addition, there are other side reactions which release water, e.g. the direct oxidation of the solvent to form by-products, and water may be added to the process for other reasons such as scrubbing offgas for solvent recovery. Typically, at least a portion of the oxidation offgas either as vapor or condensate is usually directed to a fractionation device, typically a distillation column, to separate water from the primary solvent (e.g. acetic acid) so that the water concentration in the oxidation reactor is not allowed to build up.

SUMMARY OF THE INVENTION

An objective of this invention is to provide a method for efficient and economical recovery of energy that is generated as a result of an exothermic oxidation reaction producing an aromatic carboxylic acid. Another objective of this invention is to provide for the energy recovery while also utilizing the heat from the energy of oxidation efficiently to remove water resulting from the exothermic oxidation reaction.

In one embodiment of this invention, a process for preparing aromatic carboxylic acids is provided comprising:

a). oxidizing an aromatic feedstock composition to an aromatic carboxylic acid composition in an oxidation reaction zone comprising water, a mono-carboxylic acid solvent, an oxidation catalyst composition and a source of molecular oxygen, under reaction conditions which produce an oxidation reaction offgas comprising water, gaseous by-products, and vaporized mono-carboxylic acid solvent;

b). feeding said oxidation reaction offgas from step a) directly or indirectly to an expander for recovering mechanical power producing a gaseous expander outlet product; and c). feeding said expander outlet product from step b) directly or indirectly to a fractionation zone producing a liquid containing partially de-watered mono-carboxylic acid product and producing at least one overhead aqueous product wherein the fractionation zone comprises at least two (2) theoretical stages.

In another embodiment of this invention, a process for preparing aromatic carboxylic acids is provided comprising:

a). oxidizing an aromatic feedstock composition to an aromatic carboxylic acid composition in an oxidation reaction zone comprising water, a mono-carboxylic acid solvent, an oxidation catalyst composition and a source of molecular oxygen, under reaction conditions which produce an oxidation reaction offgas comprising water, gaseous by-products, and vaporized mono-carboxylic acid solvent;

b). feeding said oxidation reaction offgas from step a) directly or indirectly to an expander for recovering mechanical power producing a gaseous expander outlet product wherein the sum total of condensable components in said oxidation reaction offgas fed to said expander is between about 65 and 85 weight percent of said oxidation reaction offgas or wherein said oxidation reaction offgas fed to said expander comprises dimers of a mono-carboxylic acid solvent in an amount of at least 9 percent based on volume of said oxidation reaction offgas fed to said expander.

DETAILED DESCRIPTION OF THE INVENTION

Figure 1:
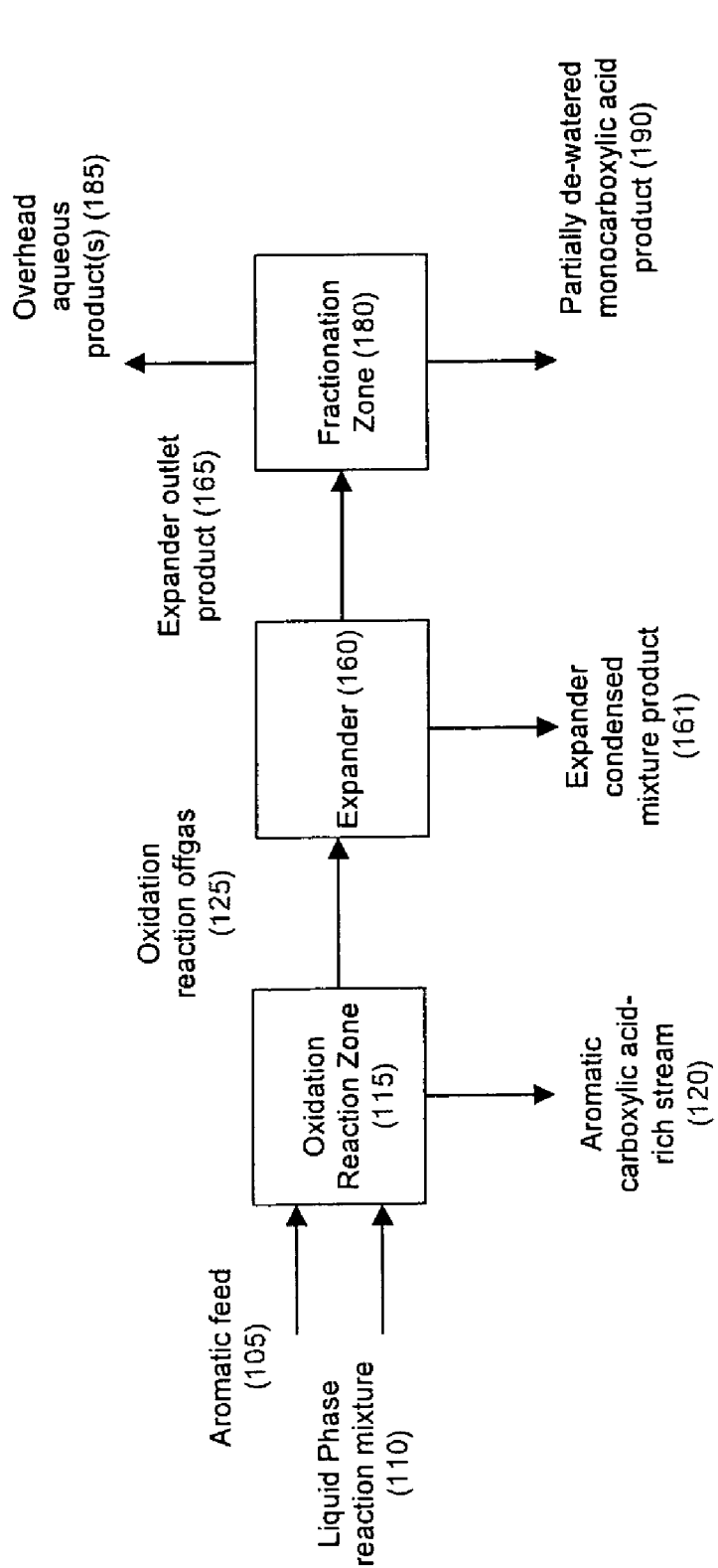
FIG. 1 illustrates embodiments of the invention where a process to efficiently recover energy from an oxidation reaction offgas and where efficient removal of the water resulting from liquid phase oxidation is provided.

In an embodiment of this invention, a process for recovery of energy and the removal of excess water from an oxidation reaction offgas 125 is provided in FIG. 1.

Step (a) comprises oxidizing an aromatic feedstock 105 with a liquid phase reaction mixture 110 in an oxidation reaction zone 115 to form an aromatic carboxylic acid-rich stream 120 and an oxidation reaction offgas 125.

The liquid phase reaction mixture 110 comprises water, a mono-carboxylic acid solvent, an oxidation catalyst composition and a source of molecular oxygen. However, if desired, one or a combination of water, mono-carboxylic acid solvent, and oxidation catalyst composition may be fed to the reaction zone separately. The reaction zone 115 may comprise at least one oxidation reactor. Oxidation is conducted under reaction conditions which produce the aromatic carboxylic acid-rich stream 120 and the oxidation reaction offgas 125. Typically, the aromatic carboxylic acid-rich stream 120 comprises a crude terephthalic acid composition.

Crude terephthalic acid is conventionally produced via the liquid phase oxidation of para-xylene in the presence of an oxidation catalyst composition and air. Suitable catalysts include, but are not limited to, cobalt, manganese, nickel, bromide compounds, and combinations thereof which are soluble in the selected solvent. Suitable solvents include, but are not limited to, aliphatic mono-carboxylic acids preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 10:1 and about 15:1. However, it should be appreciated that other suitable solvents may also be utilized.

The oxidation reaction offgas 125 is a gaseous mixture composed essentially of vaporized mono-carboxylic acid solvent, and gaseous by-products, resulting from the exothermic liquid phase oxidation reaction of an aromatic to an aromatic carboxylic acid. The oxidation reaction offgas may also comprise nitrogen and oxygen especially when air is used as the source of molecular oxygen.

The composition of oxidation reaction offgas may comprise condensable chemical compounds including, but not limited to, reaction solvent (e.g. acetic acid) and water. In one embodiment, the condensable compounds are present in the amount of at least 40, 50, or 65 weight percent up to about 85, 80, or 75 weight percent based on weight of all ingredients present in the oxidation reaction offgas. The remainder of the oxidation reaction offgas would comprise noncondensable chemical compounds, for example nitrogen, oxygen, carbon dioxide, and carbon monoxide. In the instance where a bromine compound is present in the oxidation reaction zone 115, the oxidation reaction offgas may also comprise bromine compounds such as methyl bromide which may be considered as a noncondenable chemical compound. Patents disclosing the production of terephthalic acid such as U.S. Pat. No. 4,158,738 and U.S. Pat. No. 3,996,271 are hereby fully incorporated by reference.

In one aspect of the invention, the temperature of the oxidation reaction offgas 125 is at least about 120 degrees C., 130 degrees C., or 150 degrees C. and up to about 240 degrees C., 200 degrees C. or 180 degrees C. The pressure of the oxidation reaction offgas 125 is at least about 2.5 bar gauge, 3.0 bar gauge, or 4.0 bar gauge and up to about 30 bar gauge, 10 bar gauge, or 8 bar gauge.

Step (b) comprises feeding the oxidation reaction offgas from step (a) directly or indirectly to an expander to recover at least a portion of the energy from the oxidation reaction offgas vapor. The oxidation reaction offgas 125 may be passed directly to an expander. Alternatively, a portion or all of the oxidation reaction offgas 125 may also be passed indirectly to an expander. An indirect feed of the oxidation reaction offgas to an expander excludes feeding the oxidation reaction offgas to a fractionation column which recovers greater than 95% of the mono-carboxylic acid solvent from the oxidation reaction offgas as a liquid and which produces a water-rich stream as an overhead. This fractionation device and function is performed, if at all, subsequent to the expander.

In some instances, it may advantageous or desirable to transfer at least a portion of thermal energy from the oxidation reaction offgas 125 prior to feeding the oxidation reaction offgas 125 to an expander device. For example, a portion of the thermal energy in the oxidation reaction offgas 125 can be transferred in a heat recovery device or a plurality of heat recovery devices. The transfer of thermal energy from the oxidation reaction offgas 125 can be accomplished by any means known in the art. However, generally a heat exchanger or plurality of heat exchangers can be used. Particularly well suited is a heat exchanger that functions as a vapor generator or steam generator, in which a portion of the thermal energy possessed by the oxidation reaction offgas is transferred to vaporize a suitable liquid or working fluid, for example, water or n-pentane.

As a result of this heat recovery, a condensed mixture comprising liquid solvent may be formed from a portion of the oxidation reaction offgas by partial condensation where the condensed mixture comprises less than 95% of the mono-carboxylic acid solvent in the oxidation reaction offgas. The portion or all of the oxidation reaction offgas that remains uncondensed can be passed to an expander. Any condensed mixture derived from partial condensation of the oxidation reaction offgas can be recycled back to the liquid phase oxidation reaction zone 115 either directly or indirectly.

Oxidation reaction offgas 125 is passed either directly or indirectly to an expander 160 to form an expander outlet product 165. Well-suited examples of an expander would any device that converts work from the volumetric expansion of vapor into mechanical power, a gas turbine inter alia. The expander may comprise one or more devices that convert volumetric expansion of vapor into mechanical power in a series and/or parallel configuration. The expander is suitably connected to an electrical generator and/or to other device or devices requiring mechanical power such as a compressor or pump. Electrical energy produced by a generator can be used to power the equipment used in the commercial manufacture of an aromatic carboxylic acid. For example, it can be used to operate compressors for adding air to the oxidation reaction zone. An especially well suited apparatus comprising the expander is a gas turbine with high isentropic gas expansion efficiency. Isentropic gas expansion efficiencies of greater than 70% would be preferred.

Counter intuitively, a well suited composition of the oxidation reaction offgas can advantageously contain large amount of water vapor and solvent vapors. For example, it is desirable for the sum total of condensable compounds to be at least 65 weight percent, or at least 70 weight percent, or even at least 75 weight percent of the total mass of the oxidation reaction offgas. However, the oxidation reaction offgas to remain above its dew point temperature. Typically, if the oxidation reaction offgas is below its dew point temperature, liquids or solids may become entrained in the oxidation reaction offgas thereby leading to increased corrosion and/or pitting of the expander apparatus.

In one aspect of this invention, the oxidation reaction offgas that is fed to the expander contains at least 65 weight percent water vapor and mono-carboxylic acid vapor at a temperature above its dew point. Preferably, the oxidation reaction offgas remains at temperatures above its dew point across the entire flow path through the expander apparatus. However, in the event that the oxidation reaction offgas is at or below its dew point temperature prior to the expander apparatus, here is provided another embodiment comprising a preheater to heat the oxidation reaction offgas to a temperature at or slightly above its dew point temperature. For example, a preheater may heat the oxidation reaction offgas to temperature at least 1 degrees C. above its dew point temperature. In another example, a preheater may heat the oxidation reaction offgas to temperature at least 5 degrees C. above its dew point temperature. In still another example, a preheater may heat the oxidation reaction offgas to temperature at least 20 degrees C. above its dew point temperature.

Not wishing to be bound by any theory, we believe that an oxidation reaction offgas containing large amounts of water vapor and solvent vapor is desirable because the presence of dimers and/or trimers of mono-carboxylic acids, for example acetic acid dimers, may advantageously retard the condensation of the condensable compounds in the oxidation reaction offgas. For a dilute oxidation reaction offgas composition (e.g. a gas composition with less than approximately 9 volume percent dimers, for example dimers of acetic acid), the expander outlet product temperature may be below its dew point temperature suggesting liquid formation in an expander so that substantial preheating might be required to maintain the expander outlet product above its dew point temperature.

However, when acetic acid was present at concentrations of mole percentages above 50%, modeling of the isentropic expansion accounting for the possibility for the presence of acetic acid dimers surprisingly resulted in higher expander outlet temperatures and/or lower dew point temperatures than computed for oxidation reaction offgas without acetic acid dimers. By providing an oxidation reaction offgas having large amounts of condensable compounds, and in particular mono-carboxylic acid solvent, preheating of the oxidation reactor offgas can be avoided prior to the expander, or separating the condensable compounds from the non-condensable compounds prior to the expander can be avoided, or the oxidation reaction offgas temperature can be lower thereby allowing the reaction zone to operate at a lower temperature.

Typically, the temperature the expander outlet product 165 is at least about 100, 110, or 115 degrees Celsius and up to about 200, 150, or 130 degrees Celsius. Typically pressure of the expander outlet product 165 is at least about 0.1, 0.2 or 0.5 bar gauge and up to about 7.0, 3.0, or 1.0 bar gauge.

Preferably, the temperature of the expander outlet product is above its dew temperature thereby preventing condensation. However, in the circumstances where there is some condensation, for example in a localized cold spot, an expander condensed mixture product 161 may be removed from the expander 160. This expander condensed mixture 161 product may be directly or indirectly recycled to the oxidation reaction zone or the fractionation zone 180. It is believed that whether or not the expander outlet product is above or below its dew point is a contributing factor toward corrosiveness. Corrosiveness, along with other factors, for example tensile strength and hardness, are usually also contributing factors in determining suitable materials of construction for expander devices such as gas turbines. When the expander outlet product is above its dew point temperature, the parts of the expander apparatus that are exposed to expander inlet gas and/or expander outlet product that may be suitable may comprise material of construction compositions of metals and metal alloys, for example: UNS R50400, UNS R50250, UNS R52250, UNS 53400, UNSR60702, UNS R05400, or combinations thereof. More desirably, the materials of construction compositions of metals and metal alloys may comprise for example: UNS S31803, UNS S32750, UNS N08367, UNS S31254, UNS S31000, UNS S31600, UNS N06625, UNS N10276, UNS N06200, or combinations thereof. When the expander outlet product is below its dew point temperature and especially when there is condensation, the parts of the expander apparatus that are exposed to condensation may be particularly subject to corrosion. Particularly well suited material of construction compositions of metals and metal alloys may comprise, for example UNS R50400, UNS R50250, UNS R52250, UNS 53400, UNSR60702, UNS R05400, or combinations thereof. It should be understood that the material of construction compositions referred to above uses the UNS (Unified Numbering System for Metals and Alloys) designation. The UNS system is recognized internationally and is a joint publication of the Society of Automotive Engineers (SAE) and the American Society of Testing and Materials (ASTM). The UNS provides a means of correlating many internationally used metal and alloy numbering systems currently administered by societies, trade associations, and those individual users and producers of metals and alloys.

An advantage of this invention is that the present embodiment can directly feed the oxidation reaction offgas comprising mono-carboxylic acid and water (both of which are condensing components) at or slightly above its dew point temperature to the expander whereby the recovered power is greatly increased compared to conventional methods where the condensable components are mostly removed prior to feeding into the expander.

Step (c) comprises feeding the expander outlet product 165 directly or indirectly to a fractionation zone 180 producing a liquid partially de-watered mono-carboxylic acid product 190 and producing an overhead aqueous product or overhead aqueous products 185 wherein the fractionation zone comprises at least two (2) theoretical separation stages.

The expander outlet product 165 may be passed directly to a fractionation zone 180. Alternatively, all or a portion of the expander outlet product 165 may also be passed indirectly to a fractionation zone. In some instances, it may advantageous or desirable to transfer at least a portion of thermal energy from the expander outlet product 165 prior to feeding the expander outlet product 165 to a fractionation device or apparatus. For example, a portion of the thermal energy in the expander outlet product 165 can be recovered in a heat recovery device or a plurality of heat recovery devices. The transferring of thermal energy from the expander outlet product 165 can be accomplished by any means known in the art. However, generally a heat exchanger or plurality of heat exchangers can be used. Particularly well suited is a heat exchanger that functions as a vapor generator or steam generator, in which a portion of the thermal energy possessed by the oxidation reaction offgas is transferred by vaporizing a suitable liquid or working fluid, for example, water or n-pentane.

As a result of heat recovery, a condensed mixture comprising liquid solvent may be formed from a portion of the oxidation reaction offgas by partial condensation. However, an indirect feed of the expander outlet product to a fractionation zone excludes feeding the expander outlet production to a fractionation zone which recovers greater than 95% of the mono-carboxylic acid solvent from the expander outlet product in a condensed mixture. The portion or all of the oxidation reaction offgas that remains uncondensed can be passed to a fractionation device. Any condensed mixture derived from partial condensation of the expander outlet product 165 can be recycled back to the liquid phase oxidation reaction zone 115 either directly or indirectly.

When the fractionation zone comprises a distillation column, a partially dewatered mono-carboxylic acid product, for example a partially dewatered mono-carboxylic acid product of about four (4) to twelve (12) weight percent water, can be formed from the fractionation zone. The total amount of recovered mono-carboxylic acid solvent is preferably is greater than 95% of the total feed of mono-carboxylic acid solvent to the fractionation zone 180. Most preferably, the total amount of recovered mono-carboxylic acid is greater than 98% of the total feed of mono-carboxylic acid to the fractionation zone 180. All or a portion of the partially dewatered mono-carboxylic acid product can be directly or indirectly recycled to the oxidation reaction zone 115.

The above example represents an improvement over the use of a single condenser to recover greater than 95% of the mono-carboxylic acid solvent as a partially dewatered mono-carboxylic acid product. This is partially because by utilizing more than one theoretical separation stage it is possible to obtain a partially dewatered mono-carboxylic acid product more enriched in mono-carboxylic acid solvent and an overhead aqueous product more enriched in water than can be obtained by utilizing a single condenser that is has an upper limit of one (1) theoretical separation stage.

In another example, the fractionation zone may be comprised of a distillation column or distillation columns with a plurality of trays or a suitable packing material effecting mass transfer and may have twenty (20) or more theoretical separation stages and a refluxed top section. When the fractionation zone comprises a distillation column, an overhead aqueous product or overhead aqueous product(s) can be formed from the fractionation zone 180. Desirably, the overhead aqueous product may comprise one or several streams which in total, on a continuous basis, removes a mass flow of water equivalent to or greater than the total amount of water generated by reaction in the oxidation reaction zone 115.

In still another example when the fractionation zone comprises a distillation column, a water-rich vapor may exit the upper portion of the distillation column into a condenser or partial condenser. The composition of the condensed components of the water-rich vapor collected in the condenser, known as the distillate, can be greater than about ninety-nine (99) percent water. A portion or all of the distillate can be returned as reflux to the distillation column. A portion of the distillate may be removed as an overhead aqueous product. The portion of the water-rich vapor that is not condensed, which includes most of the non-condensable components, comprise an overhead aqueous product. This vapor may be transported to a pollution control device for further treatment if desired. Additional feed material containing water (not shown) and/or mono-carboxylic acid solvent may be fed to the fractionation zone.

In distillation and/or fractionation processes, high purity distillate products are typically desired. The purity or richness of the distillate is determined partially by the amount of reflux, i.e. higher reflux ratio, richer distillate. However, if the reflux is increased, the amount of heat to operate the distillation process must also be increased. Thus, the amount of reflux that the distillation process can accommodate, as well as the purity of the distillate, is limited by the heat input provided. For example, U.S. Pat. No. 5,510,521 discloses that is there sufficient energy from oxidation reaction offgas when directly feeding to a distillation column to obtain a distillate product with above ninety-nine (99) percent water. U.S. Pat. No. 5,510,521 further indicates that such level of distillate purity is generally not attainable without additional heat sources.

In this embodiment of this invention, the inclusion of an expander after an oxidation reaction zone but before the fractionation zone changes two factors in the feasibility of separating water from mono-carboxylic acid solvent. First, the expander results in lowering the amount of energy contained within the oxidation reaction offgas by approximately the amount of energy of recovered by expander. However, in this invention, there remains sufficient energy in the fractionation feed mixture to the fractionation zone to eliminate the need for a reboiler and/or any other significant source of external heat or energy input to effect the separation of water and acid to the extent where the mass of water generated in the oxidation reaction zone is removed by the overhead aqueous product or overhead aqueous products and wherein 95% of the mono-carboxylic acid solvent in the fractionation feed mixture is recovered for reuse. Second, another factor is that the inclusion of an expander after an oxidation reaction zone but before a fractionation zone results in an increased volumetric flow to the fractionation zone due to reduction of pressure in the expander. When the fractionation zone comprises a distillation column this necessarily results in an apparatus that is larger than a corresponding apparatus not incorporating the expander to accommodate the increased volumetric flow.

Figure 2:
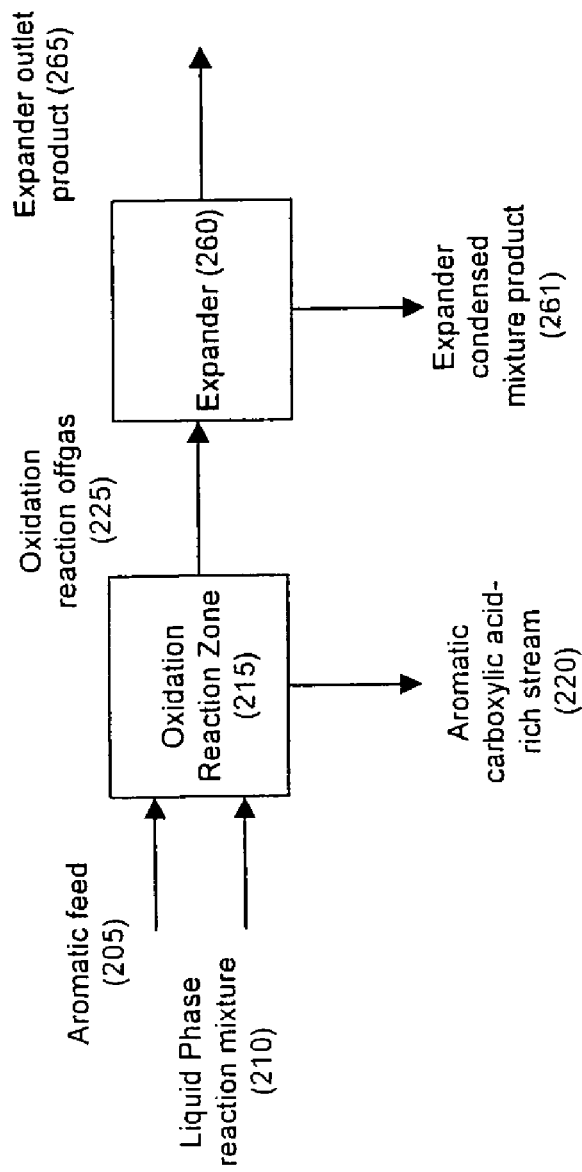
FIG. 2 illustrates embodiments of the invention where a process to efficiently recover energy from an oxidation reaction offgas is provided.

In the second embodiment of this invention, a process for recovery of energy and the removal of excess water from an oxidation reaction offgas 225 is provided in FIG. 2.

Step (a) comprises oxidizing an aromatic feedstock 205 with a liquid phase reaction mixture 210 in an oxidation reaction zone 215 to form an aromatic carboxylic acid-rich stream 220 and an oxidation reaction offgas 225.

The liquid phase reaction mixture 210 comprises water, a mono-carboxylic acid solvent, an oxidation catalyst composition and a source of molecular oxygen. However, if desired, one or a combination of water, mono-carboxylic acid solvent, and oxidation catalyst composition may be fed to the reaction zone separately. The reaction zone 215 may comprise at least one oxidation reactor. Oxidation is conducted under reaction conditions which produce the aromatic carboxylic acid-rich stream 220 and the oxidation reaction offgas 225. Typically, the aromatic carboxylic acid-rich stream 220 comprises a crude terephthalic acid composition.

Crude terephthalic acid is conventionally produced via the liquid phase oxidation of para-xylene in the presence of an oxidation catalyst composition and air. Suitable catalysts include, but are not limited to, cobalt, manganese, nickel, bromide compounds, and combinations thereof which are soluble in the selected solvent. Suitable solvents include, but are not limited to, aliphatic mono-carboxylic acids preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 10:1 and about 15:1. However, it should be appreciated that other suitable solvents may also be utilized.

The oxidation reaction offgas 225 is a gaseous mixture composed essentially of vaporized mono-carboxylic acid solvent, and gaseous by-products, resulting from the exothermic liquid phase oxidation reaction of an aromatic to an aromatic carboxylic acid. The oxidation reaction offgas may also comprise nitrogen and oxygen especially when air is used as the source of molecular oxygen.

The composition of oxidation reaction offgas may comprise condensable chemical compounds including, but not limited to, reaction solvent (e.g. acetic acid) and water. In one embodiment, the condensable compounds are present in the amount of at least 40, 50, or 65 weight percent up to about 85, 80, or 75 weight percent based on weight of all ingredients present in the oxidation reaction offgas. The remainder of the oxidation reaction offgas would comprise noncondensable chemical compounds, for example nitrogen, oxygen, carbon dioxide, and carbon monoxide. In the instance where a bromine compound is present in the oxidation reaction zone 115, the oxidation reaction offgas may also comprise bromine compounds such as methyl bromide which may be considered as a noncondenable chemical compound.

In one aspect of the invention, the temperature of the oxidation reaction offgas 125 is at least about 120 degrees C., 130 degrees C., or 150 degrees C. and up to about 240 degrees C., 200 degrees C. or 180 degrees C. The pressure of the oxidation reaction offgas 125 is at least about 2.5 bar gauge, 3.0 bar gauge, or 4.0 bar gauge and up to about 30 bar gauge, 10 bar gauge, or 8 bar gauge.

Step (b) comprises feeding the oxidation reaction offgas from step (a) directly or indirectly to an expander to recover at least a portion of the energy from the oxidation reaction offgas vapor. The oxidation reaction offgas 125 may be passed directly to an expander. Alternatively, a portion or all of the oxidation reaction offgas 125 may also be passed indirectly to an expander. An indirect feed of the oxidation reaction offgas to an expander excludes feeding the oxidation reaction offgas to a fractionation column which recovers greater than 95% of the mono-carboxylic acid solvent from the oxidation reaction offgas as a liquid and which produces a water-rich stream as an overhead. This fractionation device and function is performed, if at all, subsequent to the expander.

In some instances, it may advantageous or desirable to transfer at least a portion of thermal energy from the oxidation reaction offgas 125 prior to feeding the oxidation reaction offgas 125 to an expander device. For example, a portion of the thermal energy in the oxidation reaction offgas 125 can be transferred in a heat recovery device or a plurality of heat recovery devices. The transfer of thermal energy from the oxidation reaction offgas 125 can be accomplished by any means known in the art. However, generally a heat exchanger or plurality of heat exchangers can be used. Particularly well suited is a heat exchanger that functions as a vapor generator or steam generator, in which a portion of the thermal energy possessed by the oxidation reaction offgas is transferred to vaporize a suitable liquid or working fluid, for example, water or n-pentane.

As a result of this heat recovery, a condensed mixture comprising liquid solvent may be formed from a portion of the oxidation reaction offgas by partial condensation where the condensed mixture comprises less than 95% of the mono-carboxylic acid solvent in the oxidation reaction offgas. The portion or all of the oxidation reaction offgas that remains uncondensed can be passed to an expander. Any condensed mixture derived from partial condensation of the oxidation reaction offgas can be recycled back to the liquid phase oxidation reaction zone 115 either directly or indirectly.

Oxidation reaction offgas 125 is passed either directly or indirectly to an expander 160 to form an expander outlet product 165. Well-suited examples of an expander would any device that converts work from the volumetric expansion of vapor into mechanical power, a gas turbine inter alia. The expander may comprise one or more devices that convert volumetric expansion of vapor into mechanical power in a series and/or parallel configuration. The expander is suitably connected to an electrical generator and/or to other device or devices requiring mechanical power such as a compressor or pump. Electrical energy produced by a generator can be used to power the equipment used in the commercial manufacture of an aromatic carboxylic acid. For example, it can be used to operate compressors for adding air to the oxidation reaction zone. An especially well suited apparatus comprising the expander is a gas turbine with high isentropic gas expansion efficiency. Isentropic gas expansion efficiencies of greater than 70% would be preferred.

Counter intuitively, a well suited composition of the oxidation reaction offgas can advantageously contain large amount of water vapor and solvent vapors. For example, it is desirable for the sum total of condensable compounds to be at least 65 weight percent, or at least 70 weight percent, or even at least 75 weight percent of the total mass of the oxidation reaction offgas. However, the oxidation reaction offgas to remain above its dew point temperature. Typically, if the oxidation reaction offgas is below its dew point temperature, liquids or solids may become entrained in the oxidation reaction offgas thereby leading to increased corrosion and/or pitting of the expander apparatus.

In one aspect of this invention, the oxidation reaction offgas that is fed to the expander contains at least 65 weight percent water vapor and mono-carboxylic acid vapor at a temperature above its dew point. Preferably, the oxidation reaction offgas remains at temperatures above its dew point across the entire flow path through the expander apparatus. However, in the event that the oxidation reaction offgas is at or below its dew point temperature prior to the expander apparatus, here is provided another embodiment comprising a preheater to heat the oxidation reaction offgas to a temperature at or slightly above its dew point temperature. For example, a preheater may heat the oxidation reaction offgas to temperature at least 1 degrees C. above its dew point temperature. In another example, a preheater may heat the oxidation reaction offgas to temperature at least 5 degrees C. above its dew point temperature. In still another example, a preheater may heat the oxidation reaction offgas to temperature at least 20 degrees C. above its dew point temperature.

Not wishing to be bound by any theory, we believe that an oxidation reaction offgas containing large amounts of water vapor and solvent vapors is desirable because the presence of dimers and/or trimers of mono-carboxylic acids, for example acetic acid dimers, may advantageously retard the condensation of the condensable compounds in the oxidation reaction offgas. For a dilute oxidation reaction offgas composition (e.g. a gas composition with less than approximately 9 volume percent dimers, for example dimers of acetic acid), the expander outlet product temperature may be below its dew point temperature suggesting liquid formation in an expander so that substantial preheating might be required to maintain the expander outlet product above its dew point temperature.

However, when acetic acid was present at concentrations of mole percentages above 50%, modeling of the isentropic expansion accounting for the possibility for the presence of acetic acid dimers surprisingly resulted in higher expander outlet temperatures and lower dew point temperatures than computed for oxidation reaction offgas without acetic acid dimers. By providing an oxidation reaction offgas having large amounts of condensable compounds, and in particular mono-carboxylic acid solvent, preheating of the oxidation reactor offgas can be avoided prior to the expander, or separating the condensable compounds from the non-condensable compounds prior to the expander can be avoided, or the oxidation reaction offgas temperature can be lower thereby allowing the reaction zone to operate at a lower temperature.

Typically, the temperature the expander outlet product 165 is at least about 100, 110, or 115 degrees Celsius and up to about 200, 150, or 130 degrees Celsius. Typically pressure of the expander outlet product 165 is at least about 0.1, 0.2, or 0.5 bar gauge and up to about 7.0, 3.0, or 1.0 bar gauge.

Preferably, the temperature of the expander outlet product is above its dew temperature thereby preventing condensation. However, in the circumstances where there is some condensation, for example in a localized cold spot, an expander condensed mixture product 161 may be removed from the expander 160. This expander condensed mixture 161 product may be directly or indirectly recycled to the oxidation reaction zone or the fractionation zone 180. It is believed that whether or not the expander outlet product is above or below its dew point temperature is a contributing factor toward corrosiveness. Corrosiveness, along with other factors, for example tensile strength and hardness, are usually also contributing factors in determining suitable materials of construction for expander devices such as gas turbines. When the expander outlet product is above its dew point temperature, the parts of the expander apparatus that are exposed to expander inlet gas and/or expander outlet product that are suitable may comprise material of construction compositions of metals and metal alloys, for example: UNS R50400, UNS R50250, UNS R52250, UNS 53400, UNSR60702, UNS R05400, or combinations thereof. More desirably, the materials of construction compositions of metals and metal alloys may comprise for example: UNS S31803, UNS S32750, UNS N08367, UNS S31254, UNS S31000, UNS S31600, UNS N06625, UNS N10276, UNS N06200, or combinations thereof. When the expander outlet product is below its dew point temperature and especially when there is condensation, the parts of the expander apparatus that are exposed to condensation may be particularly subject to corrosion. Particularly well suited material of construction compositions of metals and metal alloys may comprise, for example UNS R50400, UNS R50250, UNS R52250, UNS 53400, UNSR60702, UNS R05400, or combinations thereof. It should be understood that the material of construction compositions referred to above uses the UNS (Unified Numbering System for Metals and Alloys) designation. The UNS system is recognized internationally and is a joint publication of the Society of Automotive Engineers (SAE) and the American Society of Testing and Materials (ASTM). The UNS provides a means of correlating many internationally used metal and alloy numbering systems currently administered by societies, trade associations, and those individual users and producers of metals and alloys.

An advantage of this invention is that the present embodiment can directly feed the oxidation reaction offgas comprising mono-carboxylic acid and water (both of which are condensing components) at or slightly above its dew point temperature to the expander whereby the recovered power is greatly increased compared to conventional methods where the condensable components are mostly removed prior to feeding into the expander.

The invention will now be described by the following example which is given for the purpose of illustration and is not intended to limit the scope of the invention.

EXAMPLES

Example 1

FIG. 1 shows an example of a process to efficiently recover energy from an oxidation reaction offgas and where efficient removal of the water resulting from liquid phase oxidation is provided. Results based on ASPEN Plus™ computer simulation are shown in Table 1. An oxidation reaction offgas 125 is determined/measured/generated in accordance with the diagram in FIG. 1. This oxidation reaction offgas can be produced by continuously feeding para-xylene, acetic acid solvent, oxidation catalyst (a mixture of cobalt acetate, manganese acetate, and hydrogen bromide), and air to an oxidation reaction zone (e.g. an oxidation reactor) wherein para-xylene is oxidized at a temperature of 318 degrees Fahrenheit (159 degrees Celsius) and pressure of 91.7 psia (5.3 bar gauge) yielding a mixture comprising mostly terephthalic acid and acetic acid.

The composition of the oxidation reaction offgas was determined by calculation to be composed of 58% dimers of acetic acid (i.e. 58% of the acetic acid moieties are dimers). The oxidation reaction offgas was then passed directly to an expander modeled as a near isentropic expansion with an isentropic efficiency of 80%. An expander outlet product 165 was produced with at a temperature of 253 degree Fahrenheit (123 degrees Celsius) and pressure of 29.9 psia (1.05 bar gauge). The expander outlet product was found to be 10.7 degrees Fahrenheit (5.9 degrees Celsius) above the calculated dew point temperature.

The expander outlet product was then passed directly to a distillation column modeled as an ASPEN Plus™ RADFRAC unit operation model. The RADFRAC unit operation model had approximately 38 theoretical stages. The RADFRAC also incorporated a partial column condenser above the top stage. The distillate takeoff (i.e. an overhead aqueous product) is a vapor distillate that comes from the overhead partial condenser. The overhead partial condenser condenses a portion of the incoming material to return as reflux liquid to the RADFRAC unit operation model. The RADFRAC unit operation model had 60 stages in the column with a stage efficiency of approximately 0.64. In addition to these stages, the overhead partial condenser was modeled as one theoretical stage. The vapor feed to the column is fed below the bottom stage.

The simulation model produced one overhead aqueous product streams, 185, and partially de-watered underflow mono-carboxylic acid product stream, 190. From Table 1, it can be determined that 99.995% of the acetic acid in the expander outlet product was recovered in the partially de-watered mono-carboxylic acid product stream, 190. Additionally, 67% of the water in the expander outlet product was removed by the overhead aqueous product stream.

Comparative Example 1

The computer simulation of Example 1 was re-run with the assumption that there are no dimers of acetic acid in the oxidation reaction offgas. The results of Comparative Example 1 are shown in Table 2. It is evident from the molar liquid fraction that approximately 2.62% of this stream has condensed.

Comparative Example 2

The computer simulation of Example 1 was re-run wherein the distillation column model (i.e. an ASPEN Plus™ RAD-FRAC unit operation model) was replaced with a partial condenser (i.e. an ASPEN Plus™ FLASH2 unit operation model). The results of Comparative Example 2 are shown in Table 3. This example shows that we only recover 90% of the acid that is fed to it, showing that a multi-stage distillation column is indeed superior to a partial condenser in terms of acid recovery and separation of the acid and water.

TABLE 1

| | Stream | | | |
|---|---|---|---|---|
| | 125 | 165 | 190 | 185 |
| Compound | Mass Fraction | | | |
| Nitrogen | 0.2300 | 0.2300 | 0.0001 | 0.8623 |
| Water | 0.1100 | 0.1100 | 0.1000 | 0.1375 |
| Acetic Acid | 0.6600 | 0.6600 | 0.8999 | 0.0002 |
| Total Mass | 100.0 | 100.0 | 73.3 | 26.7 |
| Temperature (degree F.) | 318 | 253 | 240 | 152 |
| Pressure (psia) | 91.7 | 29.9 | 29.9 | 20.0 |
| Molar Vapor Fraction | 1.000 | 1.000 | 0.000 | 1.000 |
| Molar Liquid Fraction | 0.000 | 0.000 | 1.000 | 0.000 |

TABLE 2

| | Stream | | | |
|---|---|---|---|---|
| | 125 | 165 | 190 | 185 |
| Compound | Mass Fraction | | | |
| Nitrogen | 0.2300 | 0.2300 | 0.0001 | 0.7876 |
| Water | 0.1100 | 0.1100 | 0.1000 | 0.1343 |
| Acetic Acid | 0.6600 | 0.6600 | 0.8999 | 0.0782 |
| Total Mass | 100.0 | 100.0 | 70.8 | 29.2 |
| Temperature (degree F.) | 325 | 246 | 238 | 158 |
| Pressure (psia) | 91.7 | 29.9 | 29.9 | 20.0 |
| Molar Vapor Fraction | 1.000 | 0.974 | 0.000 | 1.000 |
| Molar Liquid Fraction | 0.000 | 0.026 | 1.000 | 0.000 |

TABLE 3

| | Stream | | | |
|---|---|---|---|---|
| | 125 | 165 | 190 | 185 |
| Compound | Mass Fraction | | | |
| Nitrogen | 0.2300 | 0.2300 | 0.0002 | 0.7391 |
| Water | 0.1100 | 0.1100 | 0.1340 | 0.0568 |
| Acetic Acid | 0.6600 | 0.6600 | 0.8658 | 0.2041 |
| Total Mass | 100.0 | 100.0 | 68.9 | 31.1 |
| Temperature (degree F.) | 318 | 253 | 170 | 170 |
| Pressure (psia) | 91.7 | 29.9 | 29.9 | 29.9 |
| Molar Vapor Fraction | 1.000 | 1.000 | 0.000 | 1.000 |
| Molar Liquid Fraction | 0.000 | 0.000 | 1.000 | 0.000 |

We claim:

1. A continuous process for preparing aromatic carboxylic acids comprising:
   a). oxidizing an aromatic feedstock composition to an aromatic carboxylic acid composition in an oxidation reaction zone comprising water, mono-carboxylic acid solvents, an oxidation catalyst composition and a source of molecular oxygen, under reaction conditions which produce an oxidation reaction offgas comprising water, gaseous by-products, and vaporized mono-carboxylic acid solvent;
   b). feeding said oxidation reaction offgas from step a) directly or indirectly to an expander for recovering mechanical power producing a gaseous expander outlet product; and
   c). feeding said expander outlet product from step b) directly or indirectly to a fractionation zone producing a liquid containing partially de-watered mono-carboxylic acid product and producing at least one overhead aqueous product wherein the fractionation zone comprises at least two (2) theoretical stages.

2. The process of claim 1 wherein said aromatic feedstock composition comprises para-xylene and said aromatic carboxylic acid composition comprises terephthalic acid.

3. The process of claim 1 wherein said mono-carboxylic acid is acetic acid.

4. The process of claim 1 wherein said oxidation catalyst composition comprises cobalt.

5. The process of claim 1 wherein said oxidation reaction offgas feeding indirectly to said expander passes through a heat exchanger or plurality of heat exchangers transferring thermal energy to another fluid.

6. The process of claim 4 wherein said heat exchanger or plurality of heat exchanger is a steam generator.

7. The process of claim 1 wherein the sum total of condensable components in said oxidation reaction offgas is between about 40 and 85 weight percent of said oxidation reaction offgas.

8. The process of claim 1 wherein said oxidation reaction offgas is at a temperature between about 120 and 240 degrees Celsius.

9. The process of claim 1 wherein said oxidation reaction offgas is at a pressure between about 2.5 and 30 bar gauge.

10. The process of claim 1 wherein said oxidation reaction offgas comprises dimers of a mono-carboxylic acid wherein the sum total of said dimers comprises greater than 9 percent by volume of said oxidation reaction offgas.

11. The process of claim 1 wherein said expander comprises a gas turbine.

12. The process of claim 11 wherein said gas turbine is connected to a preheater.

13. The process of claim 12 wherein said preheater heats said oxidation reaction offgas to a temperature between about 1 and 20 degrees Celsius above the oxidation reaction offgas dew point temperature.

14. The process of claim 1 or 11 wherein said expander or said gas turbine is connected to an electric generator.

15. The process of claim 1 or 11 wherein said expander or said gas turbine is connected to a gas compressor or pump.

16. The process of claim 1 wherein said expander outlet product is at a temperature between about 100 and 200 degrees Celsius.

17. The process of claim 1 wherein said expander outlet product is at a pressure between about 0.1 and 7.0 bar gauge.

18. The process of claim 1 wherein said fractionation zone comprises at least one distillation column.

19. The process of claim 18 wherein said distillation column has at least twenty (20) theoretical trays.

20. The process of claim 18 wherein said fractionation zone further comprises a condenser connected to said distillation column.

21. The process of claim 1 wherein said expander outlet product feeding indirectly to said fractionation zone passes through a heat exchanger or plurality of heat exchangers transferring thermal energy to another fluid.

22. The process of claim 21 wherein said heat exchanger or plurality of heat exchanger is a steam generator.

23. A continuous process for preparing aromatic carboxylic acids comprising:
   a). oxidizing an aromatic feedstock composition to an aromatic carboxylic acid composition in an oxidation reaction zone comprising water, a mono-carboxylic acid solvent, an oxidation catalyst composition and a source of molecular oxygen, under reaction conditions which produce an oxidation reaction offgas comprising water, gaseous by-products, and vaporized mono-carboxylic acid solvent;
   b). feeding said oxidation reaction offgas from step a) directly or indirectly to an expander for recovering mechanical power producing a gaseous expander outlet product wherein the sum total of condensable components in said oxidation reaction offgas fed to said expander is between about 70 and 85 weight percent of said oxidation reaction offgas or wherein said oxidation reaction offgas fed to said expander comprises dimers of a mono-carboxylic acid solvent in an amount of at least 9 percent based on volume of said oxidation reaction offgas fed to said expander.

24. The process of claim 23 wherein said aromatic feedstock composition comprises para-xylene and said aromatic carboxylic acid composition comprises terephthalic acid.

25. The process of claim 23 wherein said mono-carboxylic acid is acetic acid.

26. The process of claim 23 wherein said oxidation catalyst composition comprises cobalt.

27. The process of claim 23 wherein said oxidation reaction offgas feeding indirectly to said expander passes through a heat exchanger or plurality of heat exchangers transferring thermal energy to another fluid.

28. The process of claim 23 wherein said heat exchanger or plurality of heat exchanger is a steam generator.

29. The process of claim 23 wherein said oxidation reaction offgas is at a temperature between about 120 and 240 degrees Celsius.

30. The process of claim 23 wherein said oxidation reaction offgas is at a pressure between about 2.5 and 30 bar gauge.

31. The process of claim 23 wherein said expander comprises a gas turbine.

32. The process of claim 23 wherein said gas turbine is connected to a preheater.

33. The process of claim 32 wherein said preheater heats said oxidation reaction offgas to a temperature between about 1 and 20 degrees Celsius above the oxidation reaction offgas dew point temperature.

34. The process of any one of claims 23 or 31 wherein said expander or said gas turbine is connected to an electric generator.

35. The process of any one of claims 23 or 31 wherein said expander or said gas turbine is connected to a gas compressor or pump.

36. The process of claim 23 wherein said expander outlet product is at a temperature between about 100 and 200 degrees Celsius.

37. The process of claim 23 wherein said expander outlet product is at a pressure between about 0.1 and 7.0 bar gauge.

38. A continuous process for preparing terephthalic acid comprising:
   a). oxidizing para-xylene to terephthalic acid in an oxidation reaction zone comprising water, acetic acid, a cobalt oxidation catalyst composition and a source of molecular oxygen, under reaction conditions which produce an oxidation reaction offgas comprising water, gaseous by-products, and vaporized acetic acid;
   b). feeding said oxidation reaction offgas from step a) directly or indirectly to an expander for recovering mechanical power producing a gaseous expander outlet product; and
   c). feeding said expander outlet product from step b) directly or indirectly to a fractionation zone producing a liquid containing partially de-watered acetic acid product and producing at least one overhead aqueous product wherein the fractionation zone comprises at least two (2) theoretical stages and the total amount of water removed by said overhead aqueous product is equal to or greater than the water generated by reaction in said oxidation reaction zone.

39. The process of claim 38 wherein said oxidation reaction offgas feeding indirectly to said expander passes through a heat exchanger or plurality of heat exchangers transferring thermal energy to another fluid.

40. The process of claim 38 wherein said heat exchanger or plurality of heat exchanger is a steam generator.

41. The process of claim 38 wherein the sum total of condensable components in said oxidation reaction offgas is between about 40 and 85 weight percent of said oxidation reaction offgas.

42. The process of claim 38 wherein said oxidation reaction offgas is at a temperature between about 120 and 240 degrees Celsius.

43. The process of claim 38 wherein said oxidation reaction offgas is at a pressure between about 2.5 and 30 bar gauge.

44. The process of claim 38 wherein said oxidation reaction offgas comprises dimers of a mono-carboxylic acid wherein the sum total of said dimers comprises greater than 9 percent by volume of said oxidation reaction offgas.

45. The process of claim 38 wherein said expander comprises a gas turbine.

46. The process of claim 38 wherein said gas turbine is connected to a preheater.

47. The process of claim 46 wherein said preheater heats said oxidation reaction offgas to a temperature between about 1 and 20 degrees Celsius above the oxidation reaction offgas dew point temperature.

48. The process of any one of claims 38 or 45 wherein said expander or said gas turbine is connected to an electric generator.

49. The process of any one of claims 38 or 45 wherein said expander or said gas turbine is connected to a gas compressor.

50. The process of claim 38 wherein said expander outlet product is at a temperature between about 100 and 200 degrees Celsius.

51. The process of claim 38 wherein said expander outlet product is at a pressure between about 0.1 and 7.0 bar gauge.

52. The process of claim 38 wherein said fractionation zone comprises at least one distillation column.

53. The process of claim 38 wherein said distillation column has at least twenty (20) theoretical trays.

54. The process of claim 53 wherein said fractionation zone further comprises a condenser connected to said distillation column.

55. The process of claim 38 wherein said expander outlet product feeding indirectly to said fractionation zone passes through a heat exchanger or plurality of heat exchangers transferring thermal energy to another fluid.

56. The process of claim 55 wherein said heat exchanger or plurality of heat exchanger is a steam generator.

* * * * *